US010088487B2

(12) United States Patent
Nagel-Steger et al.

(10) Patent No.: US 10,088,487 B2
(45) Date of Patent: Oct. 2, 2018

(54) METHOD FOR THE QUANTITATIVE CHARACTERIZATION OF AMYLOID AND/OR AGGREGATING PEPTIDES AND/OR PROTEINS IN A SAMPLE

(71) Applicant: Forschungszentrum Juelich GmbH, Juelich (DE)

(72) Inventors: Luitgard Nagel-Steger, Langenfeld (DE); Oleksandr Brener, Duesseldorf (DE); Lothar Gremer, Dormagen-Zom (DE); Dieter Willbold, Juelich (DE)

(73) Assignee: Forschungszentrum Juelich GmbH (DE)

( * ) Notice: Subject to any disclaimer, the term of this patent is extended or adjusted under 35 U.S.C. 154(b) by 34 days.

(21) Appl. No.: 14/902,754

(22) PCT Filed: Jun. 25, 2014

(86) PCT No.: PCT/DE2014/000319

§ 371 (c)(1), (2) Date: Jan. 4, 2016

(87) PCT Pub. No.: WO2015/003674

PCT Pub. Date: Jan. 15, 2015

(65) Prior Publication Data

US 2016/0349273 A1 Dec. 1, 2016

(30) Foreign Application Priority Data

Jul. 12, 2013 (DE) ........................ 10 2013 011 634

(51) Int. Cl.
*G01N 33/68* (2006.01)
*B01D 15/32* (2006.01)
*G01N 30/89* (2006.01)

(52) U.S. Cl.
CPC ....... *G01N 33/6896* (2013.01); *B01D 15/325* (2013.01); *G01N 30/89* (2013.01); *G01N 33/6845* (2013.01); *G01N 2333/4709* (2013.01); *G01N 2500/00* (2013.01); *G01N 2500/20* (2013.01); *G01N 2800/2821* (2013.01)

(58) Field of Classification Search
CPC ................... G01N 33/6896; G01N 2333/4709
See application file for complete search history.

(56) References Cited

U.S. PATENT DOCUMENTS

| | | | |
|---|---|---|---|
| 2006/0223812 | A1 | 10/2006 | Mandelkow et al. |
| 2007/0218491 | A1 | 9/2007 | Vasan et al. |
| 2009/0208960 | A1 | 8/2009 | Kelly et al. |

FOREIGN PATENT DOCUMENTS

| | | |
|---|---|---|
| WO | WO-2009/052837 | 4/2009 |
| WO | WO-2013/092951 | 6/2013 |

OTHER PUBLICATIONS

Rzepecki et al. ("Prevention of Alzheimer's Disease-associated A Aggregation by Rationally Designed Nonpeptidic-Sheet Ligands," J. Biol. Chrm).*

Stafford and Schuster ("Chapter 3, Hydrodynamic Methods" in Introduction to Biophysical Methods for Protein and Nucleic Acid Research 1995, p. 132).*

Ward et al. ("Fractionation and characterization of oligomeric, protofibrillar and fibrillar forms of -amyloid peptide," Biochem. J. (2000) 348, 137-144).*

Deguo Du et al: "A Kinetic Aggregation Assay Allowing Selective and Sensitive Amyloid-[beta] Quantification in Cells and Tissues", Biochemistry, vol. 50, No. 10, Mar. 15, 2011, (Mar. 15, 2011), pp. 1607-1617, XP055154160 ISSN: 0006-2960, DOI: 10.1021/biJ013744 Zusammenfassung: p. 1610, Spalte 1, Absatz 2; p. 1611; Figuren 1-7; ganzes Dokument.

Michael Kramer et al: "Selective detection, quantification, and subcellular location of [alpha]-synuclein aggregates with a protein aggregate filtration assay", Biotechniques, vol. 44, No. 3, Mar. 1, 2008 (Mar. 1, 2008_, pp. 403-411, XP055154158, ISSN: 0736-6205, DOI: 10.144/000112691 the whole document.

Chang, et al: "Detection and quantification of tau aggregation using a membrane filter assay", Analytical Biochemistry, Academic Press Inc., New York, vol. 373, No. 2, Jan. 5, 2008 (Jan. 5, 2008), pp. 330-336, XP 022411115, ISSN: 0003-2697, DOI: 10.1016/J.AB. 2007.09.015 the whole document.

Cheng, X.; van Breemen, R.B.: Mass Spectrometry-Based Screening for Inhibitors of B-Amyloid Protein Aggretation, In: Analytical Chemistry (2005), vol. 77, No. 21, pp. 7012-7015, Nov. 1, 2005.

Villar-Pique, A. et al.: "Using bacterial inclusion bodies to screen for amyloid aggregation inhibitors", In: Microbial Cell Factories (2012), vol. 11, Seiten 55.1-11.

Wood, S.J. et al: Selective Inhibition of AB Fibril Formation. In: The Journal of Biological Chemistry (1996), vol. 271, Nr. 8, Seiten 4086-4092.

* cited by examiner

*Primary Examiner* — Christina Bradley
(74) *Attorney, Agent, or Firm* — Jordan and Koda, PLLC

(57) ABSTRACT

A method for the quantitative characterization of amyloid and/or aggregated peptides and/or proteins in a sample, comprising:—providing a sample, wherein the sample includes an amyloid and/or aggregated peptide and/or protein having at least one aggregate size and shape;—adding an active ingredient to be analyzed to the sample solution;—separating the amyloid and/or aggregated peptides and/or proteins are from one another according to their aggregate size and shape;—optionally completely denaturing the amyloid and/or aggregated peptides and/or proteins of a particular fraction into monomer building blocks;—determining the change in concentration of the peptide and/or protein building blocks in at least one fraction by comparison against control values without the active ingredient.

19 Claims, 6 Drawing Sheets

Specification includes a Sequence Listing.

```
SEQUENCE LISTING

<160> NUMBER OF SEQ ID NOS: 2

<210> SEQ ID NO 1
<211> LENGTH: 12
<212> TYPE: PRT
<213> ORGANISM: Artificial sequence
<220> FEATURE:
<223> OTHER INFORMATION: D-peptide sequence is synthesized

<400> SEQUENCE: 1

Arg Pro Arg Thr Arg Leu His Thr His Arg Asn Arg
1               5                   10


<210> SEQ ID NO 2
<211> LENGTH: 24
<212> TYPE: PRT
<213> ORGANISM: Artificial sequence
<220> FEATURE:
<223> OTHER INFORMATION: D-peptide sequence is synthesized

<400> SEQUENCE: 2

Arg Pro Arg Thr Arg Leu His Thr His Arg Asn Arg Arg Pro Arg Thr
1               5                   10                  15

Arg Leu His Thr His Arg Asn Arg
            20
```

METHOD FOR THE QUANTITATIVE CHARACTERIZATION OF AMYLOID AND/OR AGGREGATING PEPTIDES AND/OR PROTEINS IN A SAMPLE

The invention relates to a method for the quantitative characterization of amyloid and/or aggregating peptides and/or proteins in a sample, inter alia for the quantitative determination of the effect of an active ingredient on the concentration, size and shape of aggregates of amyloid and/or aggregating peptides and/or proteins.

BACKGROUND OF THE INVENTION

No approved medicament yet exists for treating the cause of Alzheimer's dementia (AD). Deposits of the so-called beta-amyloid peptide (Aβ) in plaques are typically found post mortem in the brains of AD patients. Various forms of Aβ, for example fibrils, have therefore long been blamed for the onset and progression of AD.

For the past few years, small Aβ aggregates (Aβ oligomers) in particular have been blamed as the main culprit for the onset and progression of AD. A reduction or complete elimination of Aβ oligomers would thus appear to be the most important criterion for curing or slowing AD.

Aβ monomers are constantly being produced in our body and are presumably not toxic per se. There is speculation as to whether Aβ monomers agglomerate randomly depending on their concentration, which ultimately results from the rate at which they are formed and broken down in the body, and thus are increasingly more likely to form Aβ oligomers spontaneously as a person gets older. Once formed, Aβ oligomers could then multiply through a prion-like mechanism and ultimately lead to the disease.

Based on these considerations, causal treatment should aim at completely destroying toxic Aβ oligomers and/or hindering the prion-like multiplication thereof. One important point here is the fact that any active ingredient has to be tested in an animal model and in clinical studies. These are very time-consuming and costly. A rapid, reliable and quantitative in vitro analysis, which pre-selects the most effective active ingredients against Aβ oligomers, would be of great advantage.

Some years ago, a D-enantiomeric peptide having the name D3 was identified by a mirror image phage display selection against predominantly monomeric Aβ(1-42), with the plan of stabilizing it by way of binding and preventing the conversion thereof into toxic Aβ aggregates. According to what is presently known, D3 destroys the particularly toxic Aβ oligomers and converts these into non-toxic, non-amyloidogenic and ThT-negative amorphous aggregates. In animal models, simple oral administration of D3 with drinking water achieves a situation wherein treated transgenic AD mice exhibit considerably fewer plaques and have significantly improved cognitive capabilities.

According to the prior art, Aβ oligomers are detected and quantified for example in an Aβ-containing, non-separated sample by means of oligomer-specific antibodies. This method is only semi-quantitative because, for each sample to be determined, a comparison standard is required which necessarily must be simultaneously entrained in the assay with the sample to be measured. Furthermore, this method is not reliable because the oligomer-specific antibodies possibly do not recognize all types of oligomer or do not recognize them to the same extent.

Furthermore, an Aβ-containing sample can be fractionated with the aid of different centrifugation techniques, so that different Aβ species are present in different fractions. These can then be analyzed by means of ELISA, Western Blot or SDS-PAGE, as is known for example from Funke et al. (S. A. Funke, T. van Groen, I. Kadish, D. Bartnik, L. Nagel-Steger, O. Brener, T. Sehl, R. Batra-Safferling, C. Moriscot, G. Schoehn, A. H. C. Horn, A. Muller-Schiffmann, C. Korth, H. Sticht, D. Willbold. Oral Treatment with the D-Enantiomeric Peptide D3 Improves the Pathology and Behavior of Alzheimer's Disease Transgenic Mice. ACS Chem. Neurosci. (2010), 1, 639-648).

A third method which is often used is the ThioflavinT (ThT) test, which, however, disadvantageously, only allows a reduction in the proportion of fibrils to be measured. According to what is presently known, this is not sufficient to identify a promising active ingredient candidate for oligomer reduction.

Disadvantageously, therefore, all the techniques based on antibody detection depend on the accessibility of the epitope. On account of different Aβ aggregate structures, however, the epitopes are sometimes hidden. SDS polyacrylamide gel electrophoresis (SDS-PAGE) analyses are independent of the problems mentioned above, but disadvantageously have a lower sensitivity and are not quantitative. SDS-PAGE is moreover disadvantageous since different bands of dimers, trimers and tetramers are formed and detected, since in particular the strongly aggregating samples form aggregates of high molecular weight. Said method is thus also disadvantageously only semi-quantitative because, for each sample to be determined, a comparison standard is required which necessarily must be simultaneously entrained in the assay with the sample to be measured.

The method for the quantitative characterization of amyloid and/or aggregating peptides and/or proteins in a sample comprises the following steps:

- providing a sample, wherein the sample includes an amyloid and/or aggregating peptide and/or protein in at least one aggregate size and shape,
- adding an active ingredient to be analyzed to the sample solution,
- separating the amyloid and/or aggregating peptides and/or proteins from one another according to their aggregate size and shape. As a result, there is obtained from the sample a plurality of fractions which can be analyzed with regard to the concentration and in which the amyloid and/or aggregating peptides and/or proteins having a particular aggregate size and shape are present,
- optionally completely denaturing the amyloid and/or aggregating peptides and/or proteins of a particular fraction into monomer building blocks,
- determining the change in concentration of the peptide and/or protein building blocks by comparison against control values without the active ingredient.

The problem is also solved by the following method.

The method for the quantitative characterization of amyloid and/or aggregating peptides and/or proteins in a sample comprises the following steps:

- providing a sample, wherein the sample includes an amyloid and/or aggregating peptide and/or protein in at least one aggregate size and shape,
- adding an active ingredient to be analyzed to the sample solution,
- separating the amyloid and/or aggregating peptides and/or proteins from one another according to their aggregate size and shape to form multiple, at least 2, preferably at least 3, particularly preferably at least 4, 5, 6, 7, 8, 9, 10, 11, 12, 13, 14 or 15 fractions which can be analyzed. As a result, there is obtained from the sample a plurality of fractions which can be analyzed with regard to the concentration and in which the amyloid and/or aggregating peptides and/or proteins having a particular aggregate size and shape are present, optionally completely denaturing the amyloid and/or aggregating peptides and/or proteins of a particular fraction into monomer building blocks, determining the change in concentration of the peptide and/or protein building blocks in at least one fraction, preferably in at least 2, 3, 4, 5, 6, 7, 8, 9, 10, 11, 12, 13, 14 or 15 fractions, which can be analyzed with regard to the concentration, by comparison against control values without the active ingredient.

Advantageously, therefore, any desired fraction can be analyzed by one of the abovementioned methods to ascertain changes in concentration after the active ingredient has been added. The method thus provides a method step which makes it possible to analyze more than one fraction for changes in concentration or for changes in aggregate size or other parameters. By virtue of the method, therefore, fractions are obtained which can be analyzed both quantitatively and qualitatively, and not only in respect of changes in concentration. In the context of the method, the term "desired fraction" encompasses in particular, but not exclusively, those fractions which, prior to separation, also contained aggregating and/or aggregated peptides and/or protein building blocks, in particular toxic oligomers.

DESCRIPTION OF THE PREFERRED EMBODIMENTS

Figure 1:
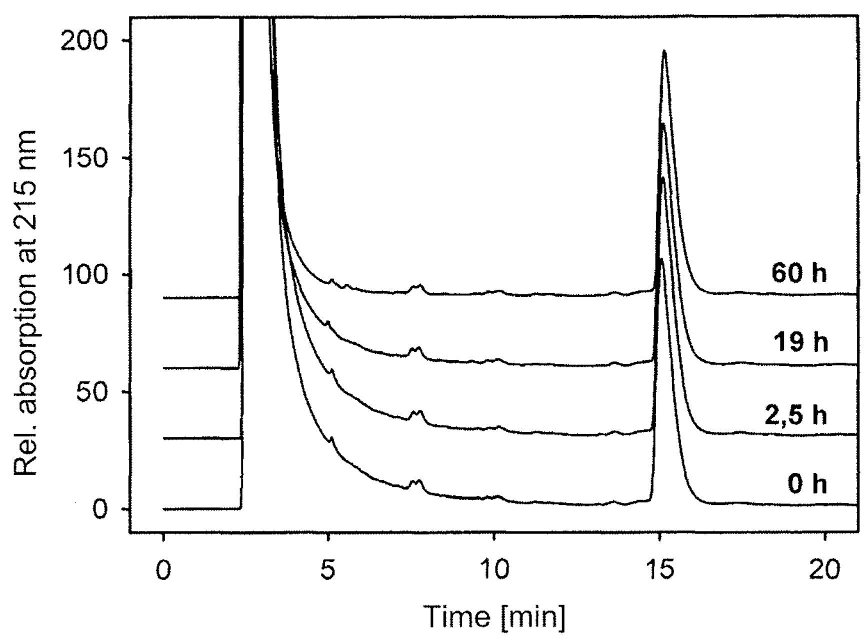
FIG. 1 shows a column chromatogram of an RP-HPLC for different aggregation states of the Aβ(1-42) peptide.

Firstly, a sample solution is prepared which includes amyloid and/or aggregating peptides and/or proteins. A sample may also be taken from another experiment, a cell culture, an animal or a human. The peptides and/or proteins have aggregation behavior. This means that, under certain conditions, the peptides and/or proteins aggregate with one another to form shapes of higher molecular weight. By way of example, mention may be made of the Aβ(1-42) peptide which occurs in Alzheimer's dementia and which has a particularly strong tendency to aggregate. Besides Aβ(1-42), other variants of Aβ also occur, for example Aβ(1-40), Aβ(1-43), Aβ(3-40), Aβ(1-40), pyroGlu-Aβ(3-40) and pyroGluAβ(3-42).

For example, a cytotoxic, oligomeric assembly of the (Aβ-)peptide and/or protein is enriched or provided, wherein a specific size distribution is set by way of pre-incubation. This advantageously means that the active ingredient to be analyzed for its effect on the particle size distribution and optionally shape distribution can be analyzed quantitatively in an exact and unambiguous manner. Even in the case of samples including aggregating Aβ(1-42), the effect of the active ingredient on the toxic Aβ oligomer species in the sample can in this way be rapidly determined.

An active ingredient is added to the sample which includes the amyloid and/or aggregating peptides and/or proteins having a different aggregate size and shape. The active ingredient changes the size distribution and thus the concentration of particular aggregates in the sample. This change in concentration is ascertained quantitatively. The change is an indication of the reduction or even of the complete elimination of particular toxic species having a detectable aggregate or particle size. That is to say that, during the method, the increase or decrease in concentration of particular amyloid and/or aggregating peptides and/or proteins is detected via the change in the aggregate size distribution.

Multiple active ingredients and the effects thereof on the sample are analyzed for a screening that is to be performed. A method for rapid pre-selection of suitable active ingredients is then advantageously provided.

The composition of amyloid and/or aggregating peptides and/or proteins having a different aggregate size and shape is therefore altered during the method under the effect of the active ingredient. While some amyloid and/or aggregating peptides and/or proteins having a particular size were initially present in the sample, these are reduced or even advantageously completely eliminated under the effect of the active ingredient. Other particle sizes increase or remain constant under the effect of the active ingredient.

The particles formed from the amyloid and/or aggregating peptides and/or proteins are separated from one another.

In this way, advantageously a plurality of fractions are obtained from the sample. The fractions contain the particles of amyloid and/or aggregating peptides and/or proteins having in each case a particular aggregate size and shape. This separation of the particles can advantageously be carried out by means of a density gradient centrifugation according to the s value. Other physical parameters of the aggregates can likewise be used as a basis for the fractionation that is to be performed, for example the hydrodynamic radius of the particles. The fractions are spatially separated from one another, for example by pipetting off. There is therefore no restriction to density gradient centrifugation. However, density gradient centrifugation has the advantage of providing all aggregates of the amyloid and/or aggregating peptides and/or proteins originally present in the sample for a further quantitative analysis. Other separating methods are suitable, such as, for example, size exclusion chromatography with separation according to the hydrodynamic radius.

Finally, the concentration of amyloid and/or aggregating peptides and/or proteins in the respective fraction is determined.

As a result, advantageously, the change in concentration of amyloid and/or aggregating peptides and/or proteins having in each case a particular size is determined quantitatively under the effect of the active ingredient. By a comparison against controls without the active ingredient, the effect of the active ingredient on the distribution of the aggregates of the amyloid and/or aggregating peptides and/ or proteins in the respective fraction can be determined quantitatively. As a result, an indication is obtained inter alia of the efficacy of the active ingredient in respect of the ability thereof to eliminate particular species from the sample, for example toxic oligomers.

It is possible to analyze a single fraction in this way. With the method according to the invention, an indication is then obtained as to the ability of the active ingredient to quantitatively modify the particular conformers from the fraction, for example to eliminate toxic oligomers from the sample.

Advantageously, therefore, a method is provided in which the change in the proportion of monomers and/or oligomers and/or fibrils and/or particularly large aggregates under the effect of the active ingredient can be determined quantitatively.

In one embodiment of the invention, the change in shape distribution of the amyloid and/or aggregating peptides and/or proteins under the effect of the active ingredient is also analyzed, for example by means of force field microscopy. In this way, in addition to the change in particle size distribution, the change in the shape distribution of the amyloid and/or aggregating peptides and/or proteins under the effect of the active ingredient is advantageously also detected, checked and/or confirmed.

In a screening method, preferably multiple active ingredients are tested in vitro for the effect on the particle size distribution of the sample. Very particularly advantageously, the method is suitable for the screening of potential active ingredients against Alzheimer's dementia (AD) based on the modulation of the toxic amyloid-β (Aβ) oligomers under the effect of the active ingredient.

The method according to the invention also provides a comprehensive, quantitative result regarding the changing particle and/or aggregate size distribution of amyloid and/or aggregating peptides and/or proteins under the effect of the active ingredient. The most promising active ingredients which lower the concentration of soluble toxic constituents such as, for example, Aβ oligomers, will thus be pre-selected for example for treating Alzheimer's dementia.

The method is not limited to this. Without limiting the method, said method also makes it possible to ascertain whether the active ingredient leads to an increase in other potentially toxic or desired species in the sample. In the case of Alzheimer's dementia, these include, for example, Aβ(1-42) monomers and/or fibrils. The method is preferably used in determining active ingredients which, according to what is presently known, do not lead to an increase in other toxic constituents. To this end, with particular advantage, several of the fractions obtained are analyzed according to the invention for a change in concentration of the building blocks.

In one particularly advantageous embodiment of the invention, a sample is prepared which includes few or no fibrils and/or larger aggregates. In this way, advantageously the formation thereof under the effect of the active ingredient can be detected particularly easily.

With particular advantage, the fractionation of the amyloid and/or aggregating peptides and/or proteins located in the sample solution takes place by means of a density gradient centrifugation using, for example, Optiprep, Percoll, sucrose or a similar density gradient material. The aggregates are in this case separated from one another according to the size and optionally the shape (sedimentation coefficient). This method is particularly advantageous in the case of aggregating Aβ(1-42) aggregates and tau aggregates.

With particular advantage, the term "precisely determined" encompasses a calibration step during the fractionation by molecules of known type and behavior. After the fractionation, only one particular (which is to say, known) type of conformer is present in each fraction, for example oligomers or fibrils and so on.

With density gradient centrifugation as the fractionation step, the conformers are separated according to their s value or sedimentation coefficient. Molecules of different size can have an identical hydrodynamic radius but nevertheless have different s values and will therefore also be separated according to this. By way of calibration with molecules of known s value, the aggregates obtained by means of density gradient centrifugation are precisely determined according to their s value.

Alternatively, a multi-stage differential centrifugation may be carried out, in which aggregates are sedimented off in stages according to their sedimentation coefficient based on the selected centrifugal force. This method is also particularly advantageous in the case of aggregating Aβ(1-42) aggregates and tau aggregates.

Alternatively, use may also be made of size exclusion chromatography, during which separation takes place according to the hydrodynamic radius. Alternatively, the fractionation takes place by asymmetric flow field-flow fractionation, or by means of capillary electrophoresis.

These methods are also suitable for the calibration.

In one very particularly advantageous embodiment of the invention, the change in concentration of amyloid and/or aggregating peptides and/or proteins having a particular size in a respective fraction is determined, after addition of the active ingredient, by complete denaturing of the amyloid peptides and/or protein building blocks during reverse phase (RP-) HPLC, which is carried out after the fractionation.

In general terms, a complete denaturing may take place via a physicochemical reaction with a denaturing agent or by way of temperature. In this way, advantageously only the monomer building blocks are supplied to the quantitative analysis.

In one very particularly advantageous embodiment of the invention, the denaturing step takes place quasi per se through column chemistry and temperature. As a result, steps are saved during processing of the sample, so that the method according to the invention can be carried out very quickly.

In principle, however, the concentration of the amyloid and/or aggregating peptides and/or proteins in the respective fraction can also be determined by isotopic labelling of the peptide and/or protein used, followed by scintillation counting of the fractions after fractionation.

In order to ascertain the effect of the active ingredient addition on oligomers that are present, the solution is therefore first incubated and then, before or after the active ingredient addition, is layered onto a pre-formed density gradient and the aggregate particles contained therein are separated accordingly by ultracentrifugation. Particle size plays an important role here. In the course of this centrifugation, in this way, for example different Aβ aggregates, such as monomers, oligomers and fibrils or amorphous aggregates, are separated from one another according to their sedimentation coefficient, which depends inter alia on the particle size. These are harvested in fractionated form.

In density gradient centrifugation, the different aggregates are separated from one another according to their s value. The larger the particle, the further it migrates into the gradient. In the harvested fractions, the concentration of the (Aβ) amyloid and/or aggregating peptide and/or protein is determined by means of RP-HPLC.

To this end, the fraction of the gradient which contains particles of corresponding size under the centrifugation conditions used is preferably completely denatured and analyzed by RP-HPLC.

The denaturing of the aggregates into monomers may take place entirely, for example, on an RP-HPLC column material such as, for example, a C8 column with approximately 30% (v/v) acetonitrile and 0.1% (v/v) trifluoroacetic acid as the mobile HPLC phase at a column temperature of approximately 80° C. The resulting monomers of the amyloid and/or aggregating peptide and/or protein are then preferably separated according to hydrophobicity by RP-HPLC. As a result, advantageously also Aβ species are separated from the density gradient material iodixanol, which due to its spectroscopic properties makes the absorption measurement of proteins impossible. Eluting peptide, such as Aβ for example, is detected by means of UV absorption at 215 nm. The peak area integration can take place by means of Agilent Chemstation software. A comparison of resulting values against the calibration that previously took place makes it possible to calculate the concentration of the peptide or protein present in the respective fraction. For each fraction, the mean value should be calculated from a plurality of, for example six, experiments carried out independently of one another with the resulting standard deviation.

The advantage of HPLC analysis lies in the fact that Aβ, for example, can then be detected very sensitively (for example approximately 20 nM or 1.8 ng Aβ(1-42) regardless of the previous aggregation state and can be reliably quantified.

One crucial advantage of the method according to the invention may therefore lie in a coupling of density gradient centrifugation and RP-HPLC, which allows a reliable quantification, in particular even of Aβ oligomers. To this end, in one advantageous embodiment of the invention, the fraction including toxic oligomers is analyzed with and without the active ingredient addition and for the change in concentration.

Surprisingly, it has been found in the context of the invention that the mobile phase used during the RP-HPLC, in combination with the increased column temperature, ensures complete denaturing of the Aβ species existing in all possible states of aggregation. A person skilled in the art is able to adapt the chemistry and temperature of the conditions of this method step so that the desired denaturing of the sample takes place.

This discovery is surprising since some of the Aβ species occurring in Alzheimer's dementia exhibit particularly high tendencies to aggregate. Even in this case, however, the denaturing of the amyloid and/or aggregating peptides and/or proteins into monomers is ensured.

It is also particularly surprising that, by means of RP-HPLC, the amyloid and/or aggregating peptide and/or protein which exists as a monomer as a result of denaturing is cleanly separated from the substance forming the density gradient, and the quantitative analysis is made accessible in a reproducible manner.

By virtue of the particularly advantageous combination of a fractionation based on density gradient centrifugation and the concentration determination by means of RP-HPLC, a method has thus been developed which particularly rapidly quantifies the effect of potential active ingredients on the proportion of toxic oligomer species of an Aβ(1-42) peptide or other peptides and/or proteins, since it is based on the monomer form.

A comparison of the control against the sample containing an active ingredient or a natural ligand allows a reproducible and rapid determination of the active ingredient efficacy with regard to eliminating and reducing particular species such as oligomers for example, and thus makes it possible to estimate the effect thereof in an animal model and subsequently in the clinical test phases. In contrast to this, the prior art describes only the possibility of quantifying the effect of one substance on the Aβ oligomer content.

With very particular advantage, however, through appropriate HPLC analysis and quantification, data is also simultaneously obtained concerning the effect of the active ingredient on increasing the amyloid and/or aggregating peptide and/or protein in other fractions, for example in fractions containing Aβ monomers and/or fibrils.

It is conceivable that, by virtue of the method according to the invention, a large number of potential active ingredients can be quantified in a rapid and reproducible manner with regard to their effect on the particle size distribution of amyloid and/or aggregating peptides and/or proteins in a sample. The sample may in this case be of synthetic nature. However, natural active ingredients or samples taken can also be analyzed in this way.

Exemplary Embodiments

The invention will be explained in greater detail below on the basis of exemplary embodiments and the appended figures, without this being intended to limit the invention in any way.

The method according to the invention was used to quantify the effect of D3 (D-enantiomer) according to SEQ ID NO: 1 on Aβ oligomers. For a screening check, a dimer of D3 was synthesized and used in the assay described above in order to check whether D3D3 (D-enantiomer) is in fact even more efficient than D3.

For the following examples of embodiments, only one ultracentrifuge and one HPLC system having a suitable separating column and a UV detector were required. In order to determine the reduction of the Aβ oligomer proportion in an aggregate mixture, pretreated and dried Aβ(1-42) peptide was dissolved in buffer and incubated until the greatest possible Aβ oligomer proportion was obtained. The active ingredient to be analyzed was then added to this oligomer-enriched sample.

Material and Methods 1 mg of lyophilized Aβ(1-42) (Bachem, Heidelberg) was incubated, after being removed from the freezer, for 10 to 30 min at room temperature (RT) in order to equalize the temperature of the peptide pellet and of the surrounding environment and thus to avoid moisture condensing from the air. Thereafter, the Aβ peptide was dissolved in HFIP (1,1,1,3,3,3-hexafluoro-2-propanol) (Sigma-Aldrich, Taufkirchen) in a concentration of 1 mg/700 μl and incubated overnight at RT with shaking until full dissolution was achieved, in order to ensure that the Aβ(1-42) exists entirely as monomers at this point in time. The Aβ(1-42) was then aliquoted in an amount of 36 μg per Eppendorf vessel. To remove the HFIP, the aliquots were left to stand open under the extractor for approximately 30 min. The rotational vacuum concentrator (rotational vacuum concentrator RVC 2-18, Christ, Mainz-Mombach) was pre-cooled for approximately 30 min. The Aβ(1-42) aliquots were then dried for a further 30 min in the rotational vacuum concentrator so that the last HFIP residues could also evaporate off. The aliquoted, dried Aβ(1-42) was stored at −20° C. until use.

Prior to the experiment, one Aβ(1-42) aliquot was dissolved to 80 μM in 100 μl of 10 mM $NaH_2PO_4/Na_2HPO_4$ buffer (Sigma-Aldrich, Taufkirchen), pH 7.4 and incubated at RT for 6 h with shaking. The incubation time of 6 h was optimized for this specific Aβ from this specific company in order to ensure that the largest possible proportion of the Aβ exists as oligomers, so as to be able to measure the reduction thereof as unambiguously as possible. For other Aβ peptides from other manufacturers, the incubation time may vary and should/can be adapted accordingly.

Thereafter, the active ingredient candidate to be analyzed was added in a quantity of 10 or 20 μM. The co-incubation of the Aβ/active ingredient solution took place for 40 min at RT with continuous shaking. When no active ingredient was added (control), the Aβ solution was treated in the same way.

The samples were then layered onto a pre-formed density gradient (see Table 1). The gradient material used consisted of a 60% strength (w/v) iodixanol solution named Optiprep™ (Axis-Shield, Oslo, Norway). It is a dimeric compound of iohexol having the systematic name 5,5-[(2-hydroxy-1,3-propanediyl)-bis(acetylimino)]bis-[N,N'-bis(2,3-hydroxypropyl)-2,4,6-triiodobenzenedicarboxamide]. The discontinuous gradient was produced by pipetting the densest Optiprep dilution onto the bottom of a polyallomer centrifuge tube (Beckman-Coulter, Palo Alto, USA) having the dimensions 11×34 mm and layering over this in stages with the less dense dilutions. The gradient adjusted to 10 mM $NaH_2PO_4/Na_2HPO_4$ buffer, pH 7.4, was composed of six stages as shown in Table 1.

TABLE 1

Volume, concentration and density of the gradient stages.

| Volume (μl) | Iodixanol (%, w/v) | Density (g/ml) |
|---|---|---|
| 100 | 5 | 1.030 |
| 260 | 10 | 1.056 |
| 780 | 20 | 1.109 |
| 260 | 30 | 1.162 |
| 260 | 40 | 1.215 |
| 260 | 50 | 1.267 |

The non-linear density gradient was centrifuged at 4° C. and 259,000×g in a TLS-55 swing-out rotor (Beckman-Coulter, Palo Alto, USA) for 3 h in a TL 100 ultracentrifuge (Beckman-Coulter, Palo Alto, USA). The density gradient is measured by refractometric determination of the iodixanol concentration in the individual fractions. An estimate of the size of sedimented protein particles based on the position in the gradient at the end of the centrifugation takes place on the basis of a calibration using marker proteins of known size and shape, which were analyzed under identical centrifugation conditions on the gradient.

The fractions were harvested from top to bottom by carefully removing them with a pipette. 14 fractions were obtained, each of 140 μl. Thus the 1st fraction was the one having the lowest density and the 14th fraction was the one having the highest density. Possibly pelleted protein was included in the analysis. 60 μl of 6 M guanidinium chloride (GdnCl) (Sigma-Aldrich, Taufkirchen) were placed in the harvested centrifuge tube and boiled for 10 min at 98° C. The pellet thus prepared represents the 15th fraction.

After fractionation of the contents of the centrifuge tube, each fraction was analyzed by means of RP-HPLC (HPLC system Agilent 1260 Infinity; quaternary HPLC pump with solvent degasser G1311B, column temperature control unit G1316A, multi wavelength detector G1365C, manual injector G1328C; Agilent, Waldbronn). A Zorbax SB-300 C8 column (5μ, 4.8×250 mm, Agilent, Waldbronn) was used as the stationary phase. The separation of the substances took place isocratically with 30% (v/v) acetonitrile, 0.1% (v/v) trifluoroacetic acid in $H_2O$ as the mobile phase at a flow rate of 1 ml/min with a column temperature of 80° C. The sample volume was 20 μl. Eluting substances were detected by means of UV absorption at 215 nm. Data recording and peak area integration took place by means of Agilent Chemstation software (Agilent, Waldbronn). Using RP-HPLC, the density gradient material iodixanol present in the fractions is separated from the Aβ(1-42) peptide. Only by virtue of this separation is it possible to detect Aβ spectroscopically, since without separation the strong absorption of the iodixanol in the UV range hides the absorption of the Aβ peptide.

The determination of the molar Aβ concentrations took place by means of a calibration of the column with Aβ solutions having known concentrations (Aβ dilution series). The regression line adapted to the linear relationship between area and peptide concentration has a coefficient of determination $R^2$ of 0.998. Due to this quantification, it is possible to calculate the recovery rate of the applied Aβ42 peptide for each run. For this purpose, the molar concentrations determined for each fraction are summed in a manner converted to mol/fraction by multiplying by the fraction volume $140\times10^{-6}$ l (fractions 1 to 14) and $120\times10^{-6}$ l (fraction 15). The quotient of this sum and of the number of moles of Aβ peptide contained in the applied sample gives the recovery rate R as a percentage.

$$R = \frac{c_P V_P + \sum_{n=1}^{14} c_n \cdot V_F}{c_0 \cdot V_0}$$

Here, $c_p$ is the molar concentration of Aβ in the pellet, $c_n$ is the molar concentration of Aβ in fractions 1 to 14, $c_0$ is the molar concentration of Aβ prior to DGC, $V_F$ is the fraction volume ($140\times10^{-6}$ l), $V_P$ is the volume of the pellet fraction ($120\times10^{-6}$ l) and $V_0$ is the sample volume prior to DGC ($100\times10^{-6}$ l).

The recovery rate was between 0.8 and 1.0 or between 80 and 100%. The high recovery rate ensures that the data obtained reflect the state of the sample as a whole and do not describe only a portion of the sample.

The advantage of the RP-HPLC method over other methods lies in the fact that the quantification of the Abeta peptide is independent of its previous aggregation state, that is to say monomer, oligomer or fibrils. This is not guaranteed, for example, in the case of immunochemical detection methods since, due to the aggregation, the antibody-binding epitopes may not be as accessible or may even not be accessible at all.

It has been found that the denaturing of the Aβ 1-42 particles present in any form in the sample always leads to monomers. With particular advantage, these can be quantified regardless of the original structure. As a result, the different species such as oligomers, fibrils and amorphous aggregates are always reliably quantified as monomers in a reproducible manner.

Results

FIG. 1 shows column chromatograms of an RP-HPLC for different aggregation states of the Aβ(1-42) peptide. For each sample, 20 μl of solution containing 1.8 ng of Aβ(1-42) were injected onto a C8 column (5μ, 4.8×250 mm) and eluted with 30% (v/v) acetonitrile, 0.1% (v/v) trifluoroacetic acid in $H_2O$ as eluent with a flow rate of ml/min at a column temperature of 80° C. The relative absorption at 215 nm of the eluate is plotted against the retention time for freshly dissolved (0 h) Aβ(1-42) and Aβ(1-42) that had been pre-incubated for 2.5 h, 19 h and 60 h, which was adjusted to 40% (w/v) iodixanol in order to simulate the conditions of the density gradient. Iodixanol elutes considerably before Aβ(1-42) with a retention time of between 2 and 5 min. The chromatogram clearly documents the perfect separation of the iodixanol, which hinders detection of the Aβ in the UV range, and the reproducible quantification of the Aβ peptide regardless of whether it was present in the sample as a monomer, oligomer or as fibrils.

Figure 2:
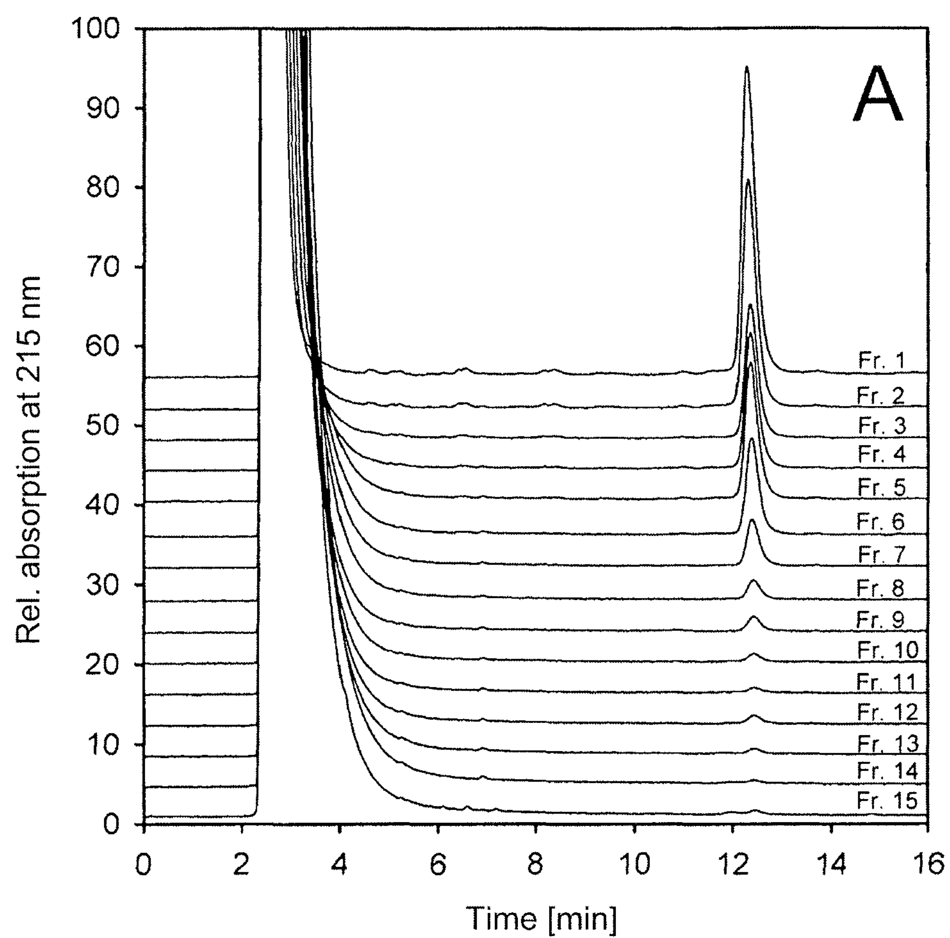
FIG. 2 shows chromatograms of the RP-HPLC for fractions 1 to 15 of a density gradient with the concentrations calculated therefrom for each fraction.
Figure 2:
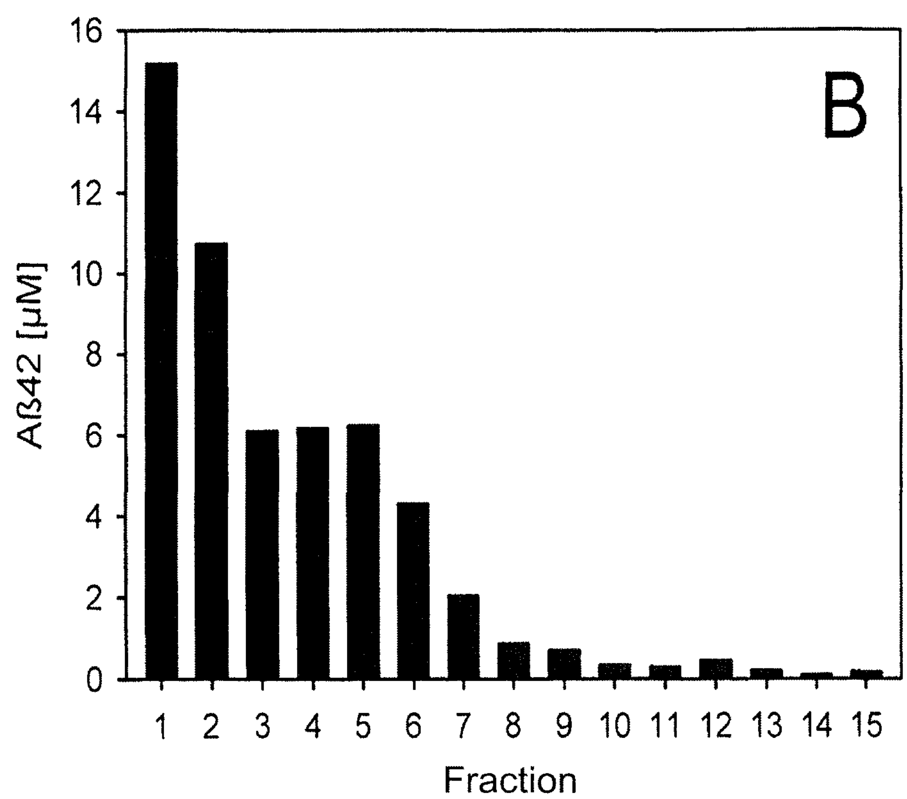

FIG. 2 shows chromatograms of the RP-HPLC for fractions 1 to 15 of a density gradient, with the concentrations calculated therefrom for each fraction. After preparing an oligomer-enriched Aβ(1-42) sample, the latter is layered onto an iodixanol density gradient and centrifuged at 259,000 g for 3 h at 4° C. During this, different Aβ aggregates are separated from one another according to their s value. The larger the particle, the further it migrates into the gradient. In the 14 fractions of pi harvested from top to bottom and in the pellet (fraction 15) boiled with 60 μl of 6 M GdnCl, the concentration of the Aβ(1-42) peptide is determined by means of RP-HPLC. To this end, 20 μl of each fraction are completely denatured on a C8 with 30% (v/v) acetonitrile and 0.1% (v/v) trifluoroacetic acid at a column temperature of 80° C. and separated according to hydrophobicity. In the process, the Aβ(1-42) is separated from the density gradient material iodixanol, which, due to its spectroscopic properties, makes absorption measurement of proteins impossible. Eluting Aβ(1-42) is detected by means of UV absorption at 215 nm. Peak area integration takes place by means of Agilent Chemstation software. Comparison of resulting values against the previously performed calibration makes it possible to calculate the concentration of the Aβ peptide present in the respective fraction. As shown previously in FIG. 1, here the elution curves for all the harvested fractions of a density gradient are now summarized in one FIG. (A). The constancy of the retention time for the Aβ(1-42) regardless of the position in the gradient and thus of the state of aggregation of the peptide is important. Diagram (B) shows the Aβ concentrations in μmol/liter calculated from the peak areas on the basis of the calibration lines determined for the column.

Figure 3:
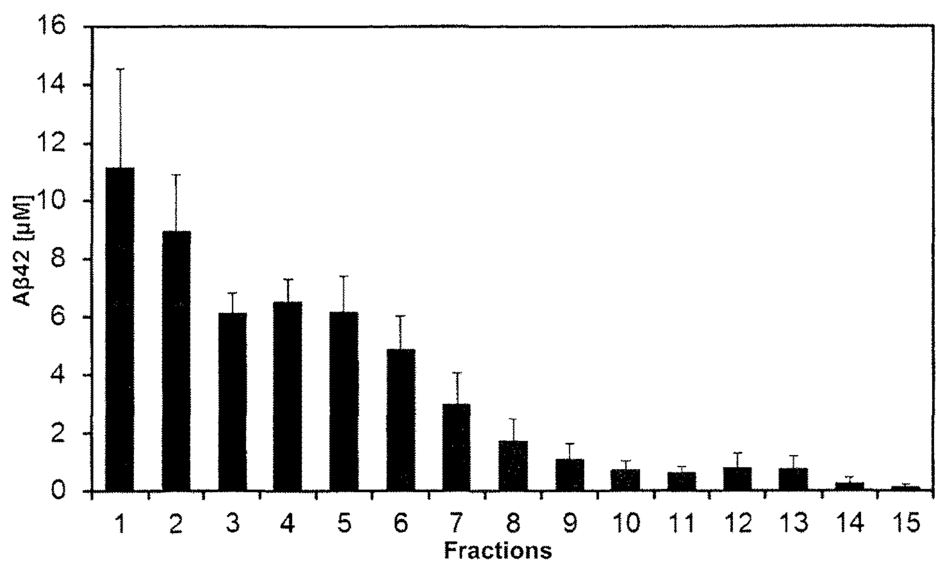
FIG. 3 shows the averaged size distribution for six Aβ(1-42) controls without active ingredient addition after density gradient centrifugation and RP-HPLC.

FIG. 3 shows the averaged size distribution for six Aβ(1-42) controls without active ingredient addition after density gradient centrifugation and RP-HPLC. In each case, the average value from six experiments carried out independently of one another is shown for each fraction, with the resulting standard deviation. In the first fractions, the Aβ(1-42) peptide which existed as a monomer at the time of fractionation is again found. Oligomers of the Aβ(1-42) peptide can clearly be seen in fractions 4 to 6, said oligomers being formed during pre-incubation. Based on their position in the gradient and the comparison against proteins of known s values, these have an s value of approximately 5 S. Based on the s value and under the assumption of a globular shape, these oligomers are composed of approximately 20 monomeric units. Force-field microscopy analyses were able to confirm the globular shape of these particles. Toxicity tests using the fractionated oligomers demonstrated the neurotoxic properties thereof. By virtue of the combination of density gradient fractionation and concentration determination by means of RP-HPLC, a method has been developed which makes it possible to analyze the effect of potential active ingredients on the amount of a toxic oligomer species of the Aβ(1-42) peptide fractions of Aβ oligomers in a sample and effects on the quantity thereof by potential active ingredients.

Figure 4:
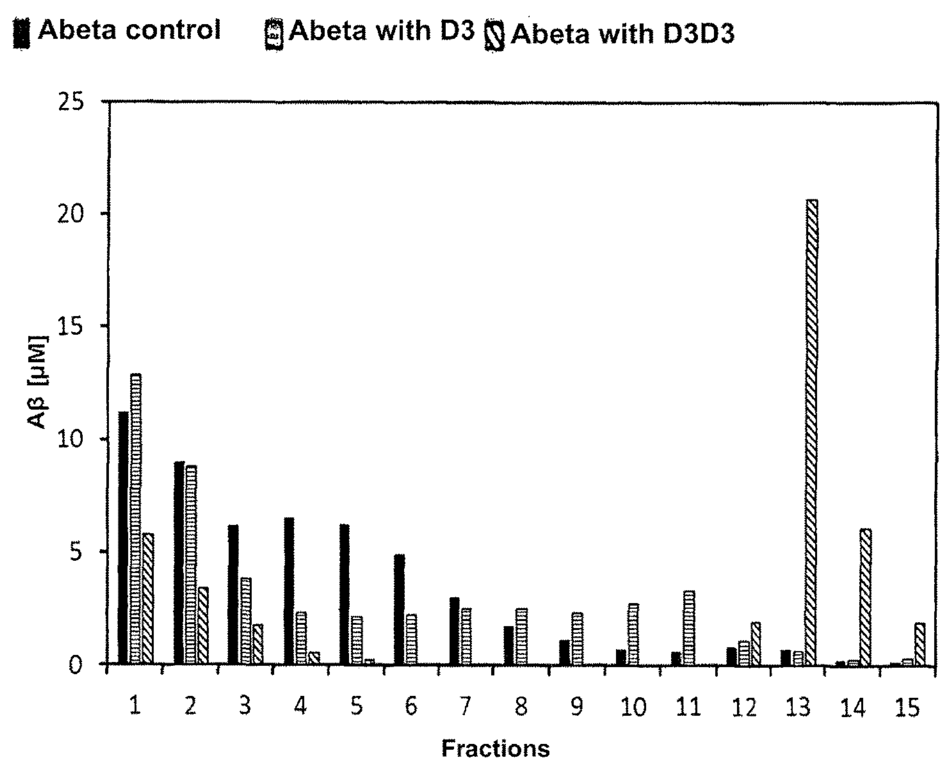
FIG. 4 shows the use of the described method for analyzing potential active ingredients for treating Alzheimer's dementia, based on the example of a D-peptide (D3) and its tandem dimer (D3D3).

FIG. 4 shows the use of the described method in order to analyze potential active ingredients for treating Alzheimer's dementia based on the example of a D-peptide (D3) and its tandem dimer (D3D3). The diagram shows the effect of 20 μM of D3 to SEQ ID NO: 1 and 10 μM of D3D3 according to SEQ ID NO: 2 on the size distribution of the Aβ(1-42) aggregates in a density gradient. After preparing an oligomer-rich Aβ sample, the active ingredient to be tested is added. After incubating for 40 minutes, this mixture is layered onto an iodixanol density gradient and centrifuged at 259,000 g for 3 h at 4° C. An identically treated Aβ(1-42) solution without the active ingredient addition is used as the control. By virtue of the centrifugation, different Aβ aggregates are separated according to their sedimentation coefficient (s value). The greater the s value of the particle, the further it migrates into the gradient. The gradient is then manually fractioned from top to bottom. This results in 14 fractions of 140 μl each, and one 60 μl pellet fraction which is boiled with 60 μl of 6 M GdnHCl. Aβ oligomers, consisting of approximately 20 units (s value is approximately 5 S) are recovered in fractions 4 to 6. For each gradient, in each case a 20 μl aliquot of all fractions is analyzed by means of RP-HPLC. In order to determine the Aβ concentration per fraction, Aβ in the aliquot is completely denatured on a C8 column having a mobile phase consisting of 30% (v/v) acetonitrile and 0.1% (v/v) trifluoroacetic acid at a column temperature of 80° C. and is separated off from the density gradient material iodixanol and the active ingredient so that it can be detected by its UV absorption at 215 nm and quantified. The data recording and peak area integration take place using the Agilent Chemstation software (Agilent, Waldbronn). The concentration data thus obtained are plotted in the diagram against the fraction numbers. In fractions 4 to 6, which contain oligomeric Aβ species, the addition of D3 and D3D3 led to a reduction in the quantity of oligomers. D3D3, which was used in only half as concentrated a form in comparison to D3, exhibits a much more pronounced effect in this test system than D3 in terms of eliminating oligomeric Aβ species. The proportion of large aggregates in fractions 11 to 14 is much greater under the effect of the active ingredients, in particular in the case of D3D3. The combination of density gradient and RP-HPLC therefore represents a novel method for screening active ingredients for treating Alzheimer's dementia and for the quantitative characterization of amyloid and/or aggregating peptides and/or proteins, which uses the ability to eliminate Aβ oligomers as a novel selection criterion.

Figure 5:
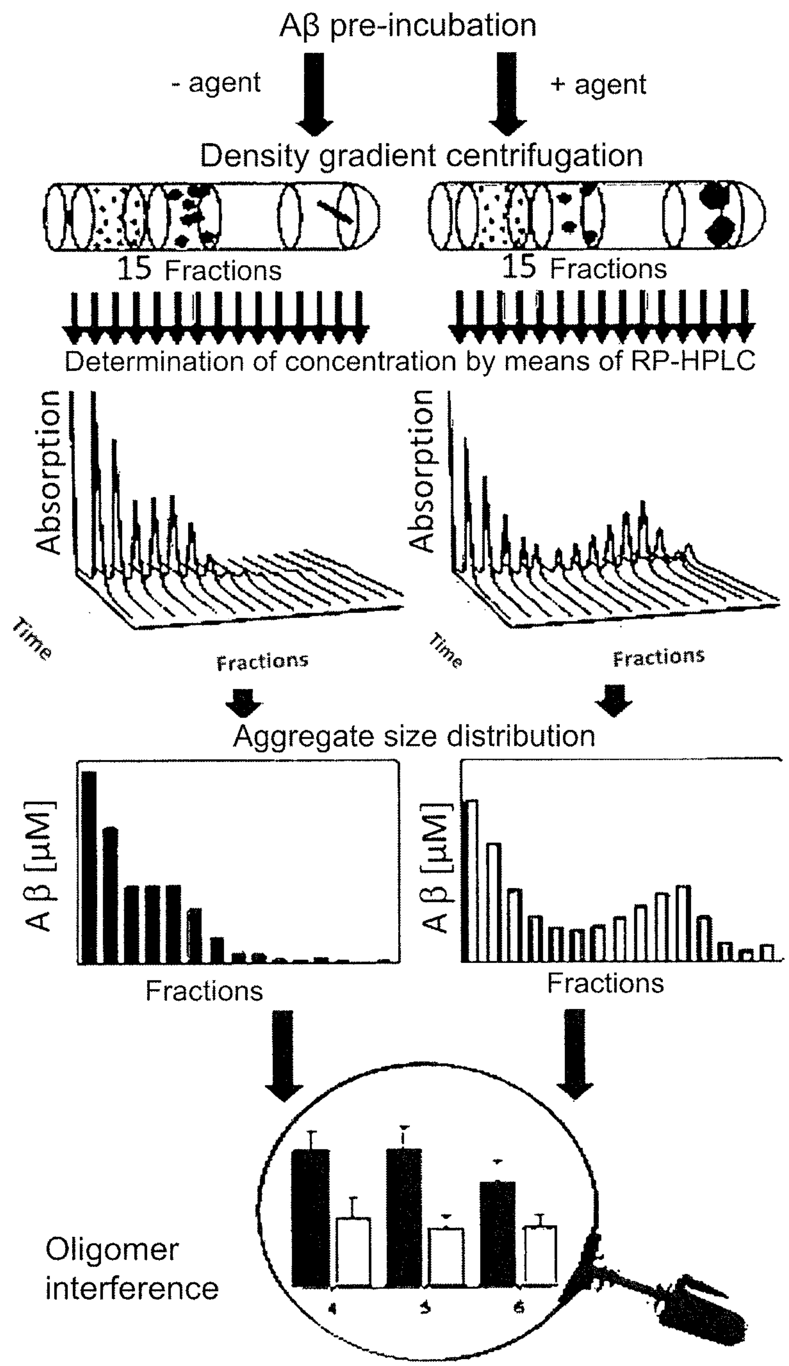
FIG. 5 shows an experimental approach for the quantitative characterization of amyloid and/or aggregating Aβ without and with active ingredient, and for ascertaining the change in concentration of monomers in different fractions after denaturing during and with the RP-HPLC and active ingredient addition.

FIG. 5 schematically shows one embodiment of the method according to the invention in brief. After pre-incubating Aβ, the sample is further analyzed in a batch with and without the addition of active ingredient. After separating into 15 fractions by means of density gradient centrifugation and after denaturing, the concentration of monomer building blocks in preferably all 15 fractions is determined during RP-HPLC, and in particular the effect of the active ingredient on the oligomer concentration is determined.

The sequence listings for SEQ ID NO. 1 and SEQ ID NO. 2, as found in the 1 kb text file named 'F11570SequenceListing04.txt' created and uploaded to EFS-Web on Aug. 9, 2016 are incorporated herein by reference.

The invention claimed is:

1. A method for quantitatively determining an effect of an active ingredient on a concentration of amyloid and/or aggregating peptides and/or proteins in a sample solution, comprising the steps of:

providing a sample in the sample solution, wherein the sample includes said amyloid and/or aggregating peptide and/or proteins having at least one aggregate size and shape;

adding said active ingredient to the sample solution;

separating the amyloid and/or aggregating peptides and/or proteins from one another according to their aggregate size and shape by density gradient centrifugation to achieve fractionation of the sample into a plurality of fractions;

completely denaturing the amyloid and/or aggregated peptides and/or proteins of a first fraction among said plurality of fractions into monomer building blocks; and after said completely denaturing, determining a change in concentration of peptides and/or proteins among the amyloid and/or aggregated peptides and/or proteins of said first fraction by a comparison against control values without the active ingredient.

2. The method according to claim 1 wherein multiple active ingredients are tested in a screening process in vitro.

3. The method according to claim 1, wherein said provided sample contains a plurality of aggregate sizes which become separated into said plurality of fractions, and said determining step comprising determining said change in concentration for each one fraction of said plurality of fractions.

4. The method according to claim 1, wherein said separating comprises performing said density gradient centrifugation with calibration to obtain fractionation of the prepared sample.

5. The method according to claim 1, wherein said density gradient centrifugation is calibrated, according to a sedimentation coefficient, for performing said separating.

6. The method according to claim 1, wherein said determining comprises determining using reverse phase (RP-) HPLC.

7. The method according to claim 6, wherein said completely denaturing occurs during the reverse phase (RP-) HPLC, prior to said determining said change in concentration, the amyloid and/or aggregated peptides and/or proteins being completely denatured into monomers based upon a choice of mobile phase and/or a choice of column temperature of the reverse phase (RP-) HPLC.

8. The method according to claim 1, wherein upon said separating said plurality of fractions are situated according to a density gradient, and further comprising performing a reverse phase (RP-) HPLC, wherein a mobile phase for said reverse phase (RP-) HPLC is chosen which provides separation of the amyloid and/or aggregated peptides and/or proteins for each fraction of said plurality of fractions of said density gradient.

9. The method according to claim 1, wherein during the method, a sample is provided in which an aggregating Aβ is included from among a group comprising Aβ(1-40), Aβ(1-42), Aβ(1-43), Aβ(3-40), pyroGluAβ(3-40), pyroGluAβ(3-42), tau protein or another peptide typically occurring in Alzheimer's dementia and having a high tendency to aggregate.

10. The method according to claim 1, further comprising, after said separating, determining a change in shape distribution of the amyloid and/or aggregated peptides and/or proteins in said first fraction as an effect of said active ingredient.

11. The method according to claim 10, wherein said change in shape distribution is determined using force field microscopy or electron microscopy or the like.

12. The method according to claim 1, wherein said provided sample includes said amyloid and/or aggregating peptide and/or proteins having a plurality of aggregate sizes and shapes;

wherein said completely denaturing comprises completely denaturing the amyloid and/or aggregated peptides and/or proteins of each one fraction of multiple fractions among said plurality of fractions into monomer building blocks; and wherein said determining comprises determining a change in concentration of peptides and/or proteins among the amyloid and/or aggregated peptides and/or proteins of each one fraction of said multiple fractions by a comparison against control values without the active ingredient.

13. The method according to claim 12, wherein said determining said change in concentration comprises determining the change in concentration of monomers and/or oligomers and/or fibrils and/or other conformers of each one fraction of said multiple fractions under the effect of the active ingredient.

14. The method according to claim 1, wherein said active ingredient has an effect on said provided sample in said sample solution of minimizing toxic molecules formed so as to treat a protein mis-folding disease.

15. The method according to claim 1, wherein the amyloid and/or aggregated peptides and/or proteins are separated from one another according to aggregate size and shape to form 2, 3, 4, 5, 6, 7, 8, 9, 10, 11, 12, 13, 14 or 15 fractions which can be analyzed.

16. The method according to claim 1, wherein said determining comprises determining said change in concentration of peptides and/or proteins among the amyloid and/or aggregated peptides and/or proteins of multiple fractions among said plurality of fractions by comparison against control values without the active ingredient.

17. The method according to claim 1, wherein a concentration of peptides and/or proteins among the amyloid and/or aggregated peptides and/or proteins prior to said separating is known, and further comprising deriving a recovery rate for said peptides and/or proteins among the amyloid and/or aggregated peptides and/or proteins by comparing the concentrations known prior to said separating to the concentrations determined in said determining step.

18. The method according to claim 1, wherein said determining the change in concentration is performed for each one fraction of the plurality of fractions, the change in concentration within each one fraction of the plurality of fractions being based on a comparison against at least one control sample in sample solution without the active ingredient.

19. The method according to claim 1, wherein each one fraction of said plurality of fractions of the sample resulting from said density gradient centrifugation is characterized by an aggregation state of the the amyloid and/or aggregating peptides and/or proteins; and wherein said completely denaturing is achieved by reverse phase (RP-) HPLC for each one fraction of the plurality of fractions, said reverse phase (RP-) HPLC being effective to completely denature into monomers the amyloid and/or aggregated peptides and/or proteins of each one fraction of the plurality of fractions, regardless of the aggregation state, based upon a choice of mobile phase and/or a choice of column temperature of the reverse phase (RP-) HPLC.

* * * * *